US008535739B2

(12) United States Patent
Lowe

(10) Patent No.: US 8,535,739 B2
(45) Date of Patent: Sep. 17, 2013

(54) SPARKLE ESSENCE SYSTEM

(76) Inventor: George Lowe, Toronto (CA)

( * ) Notice: Subject to any disclaimer, the term of this patent is extended or adjusted under 35 U.S.C. 154(b) by 89 days.

(21) Appl. No.: 13/011,218

(22) Filed: Jan. 21, 2011

(65) Prior Publication Data

US 2011/0180431 A1 Jul. 28, 2011

Related U.S. Application Data

(60) Provisional application No. 61/298,964, filed on Jan. 28, 2010.

(51) Int. Cl.
*A61K 36/00* (2006.01)

(52) U.S. Cl.
USPC .......................................... 424/774; 424/725

(58) Field of Classification Search
None
See application file for complete search history.

(56) References Cited

U.S. PATENT DOCUMENTS

| | | | | |
|---|---|---|---|---|
| 1,675,227 | A | 6/1928 | Reeve | |
| 4,308,047 | A | 12/1981 | Holland | |
| 4,810,421 | A | 3/1989 | Marchesini | |
| 5,503,766 | A | 4/1996 | Kulperger | |
| 5,849,682 | A | 12/1998 | Van Eenam | |
| 6,090,765 | A | 7/2000 | Black et al. | |
| 6,552,085 | B2 * | 4/2003 | Inman et al. | 514/576 |
| 6,797,285 | B1 * | 9/2004 | Yuan | 424/725 |
| 7,763,292 | B2 * | 7/2010 | Gutierrez-Uribe et al. | 424/757 |
| 2002/0058708 | A1 * | 5/2002 | Inman et al. | 514/568 |
| 2004/0170704 | A1 * | 9/2004 | Tze et al. | 424/725 |
| 2004/0191190 | A1 * | 9/2004 | Pauly et al. | 424/59 |
| 2007/0077308 | A1 * | 4/2007 | Giner | 424/490 |

FOREIGN PATENT DOCUMENTS

| | | | |
|---|---|---|---|
| CN | 1489942 | * | 4/2004 |
| CN | 1772033 | * | 5/2006 |

OTHER PUBLICATIONS

Jaiswal et al. Indian J. Clin. Biochem. 2008. vol. 23, No. 2, pp. 167-170.*
Iwu et al. Handbook of African Medicinal Plants. 1993. CRC Press, pp. 137-138.*
Ezeifeka et al. Biotechnol. 2004. vol. 3, No. 1, pp. 41-43.*

* cited by examiner

*Primary Examiner* — Chris R Tate
(74) *Attorney, Agent, or Firm* — RG Patent Consulting LLC; Rachel Gilboy

(57) ABSTRACT

A plant-based cleaning agent for household use designed to produce optimal cleaning results. This product is comprised of pigeon pea extract and distilled water. To create the proper mixture, 12 g of pigeon pea leaves may be cut up and placed in a beaker, wherein the pigeon pea leaves homogenize with 2000 ml of distilled water. The mixture is centrifuged at 8,000 rpm for ten minutes. The pellet is then discarded and the extract is stored at approximately 4 degrees C. for about forty-eight hours. Stability is achieved by putting the extract through a 0.45 um filter. For use, consumers spray the sparkle essence product onto a desired glass surface and wipe away with a cloth or paper towel.

5 Claims, 2 Drawing Sheets

SPARKLE ESSENCE SYSTEM

CROSS-REFERENCE TO RELATED APPLICATION

The present application is related to and claims priority from prior provisional application Ser. No. 61/298,964 that was filed on Jan. 28, 2010 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. FIELD OF THE INVENTION

The present invention relates generally to the field of cleaning agents and more specifically relates to a plant-based cleaning agent for household use, entitled Sparkle Essence.

2. DESCRIPTION OF THE RELATED ART

Hard surface cleaners is a category of cleaning agents comprising mainly aqueous solutions of specialty chemicals that vary with the amount of dirt and the surface being cleaned. Light duty hard surface cleaners are not intended to handle heavy dirt and grease. Because these products are expected to clean without rinsing and result in a streak-free shine, they normally contain no salts. Typical window cleaners consist of alcohols, either ethanol or isopropanol (rubbing alcohol) and surfactants for dissolving grease. Other components may include small amounts of ammonia as well as dyes and perfumes.

Many household cleaners may deliver only marginal cleaning effectiveness. Glass cleaners in particular can leave streaks after use, thereby causing glass surfaces to lose translucence and to appear dirty. More substantial cleaners may work slightly better, but may also be filled with harsh chemicals. Using these kinds of cleaners can inflict harm on the environment. Further, these products may also pose serious health concerns for children or pets, who may accidentally ingest or inhale large quantities of these type of cleaning agents. Such ingestion and even inhalation by the very young may cause severe illness and possibly death. Therefore a need exists for an all-natural plant ingredient based cleaning agent for household use that is void of harmful chemicals.

Various attempts have been made to solve the above-mentioned problems such as those found in U.S. Pat. Nos. 4,308,047; 5,503,766; 1,675,227; 4,810,421; 5,849,682; and 6,090,765. This prior art is representative of cleaners. None of the above inventions and patents, taken either singly or in combination, is seen to describe the invention as claimed.

Ideally, a plant-based cleaning agent for household use should be safe to use and, yet would operate reliably and be manufactured at a modest expense. Thus, a need exists for a reliable all-natural plant ingredient based cleaning agent that is void of harmful chemicals. and to avoid the above-mentioned problems.

BRIEF SUMMARY OF THE INVENTION

In view of the foregoing disadvantages inherent in the known household cleaning agent art, the present invention provides a novel sparkle essence system. The general purpose of the present invention, which will be described subsequently in greater detail is to provide a sparkle essence system comprising a plant-based cleaning agent designed for safe household use. This innovative product features all-natural plant ingredients and is void of harmful chemicals. This novel mixture can be used on a variety of glass surfaces, such as home windows, car windows, glass headlights, television screens, computer screens, and can also be used on select surfaces comprising other materials. Consumers may use the sparkle essence system to thoroughly clean their homes without the risk of harming children, pets, or the environment.

A plant-based household cleaner is disclosed herein preferably comprising ingredients combined in proportions substantially including: 12 g of pigeon pea leaves; and 2000 mL of distilled water. The plant-based household cleaner may be prepared by cutting and placing the pigeon pea leaves in a beaker comprising distilled water to create a homogenized mixture in a centrifuge.

The plant-based household cleaner is centrifuge-processed using the centrifuge at about 8,000 rpm for approximately ten minutes. After the centrifuge is used, a pellet is formed and is discarded so a newly formed extract is able to be stored at approximately 4 degrees C. for forty-eight hours to achieve stability by putting the newly formed extract through a 0.45 um filter.

A kit is also embodied herein for the sparkle essence system comprising: the plant-based household cleaner; at least one spray bottle; and a set of user instructions for making and using the cleaner.

A method of producing the sparkle essence system is also disclosed herein comprising the steps of: step one intermixing 12 g of pigeon pea leaves and 2000 mL of distilled water thereby producing mixture; step two sealingly storing mixture within at least one spray bottle; and spraying plant-based household cleaner using a spray bottle with a nozzle.

The present invention holds significant improvements and serves as a sparkle essence natural cleaning system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, sparkle essence system, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a cleaning agent and more particularly to a plant-based environmentally-friendly cleaning agent for household use.

Figure 1:
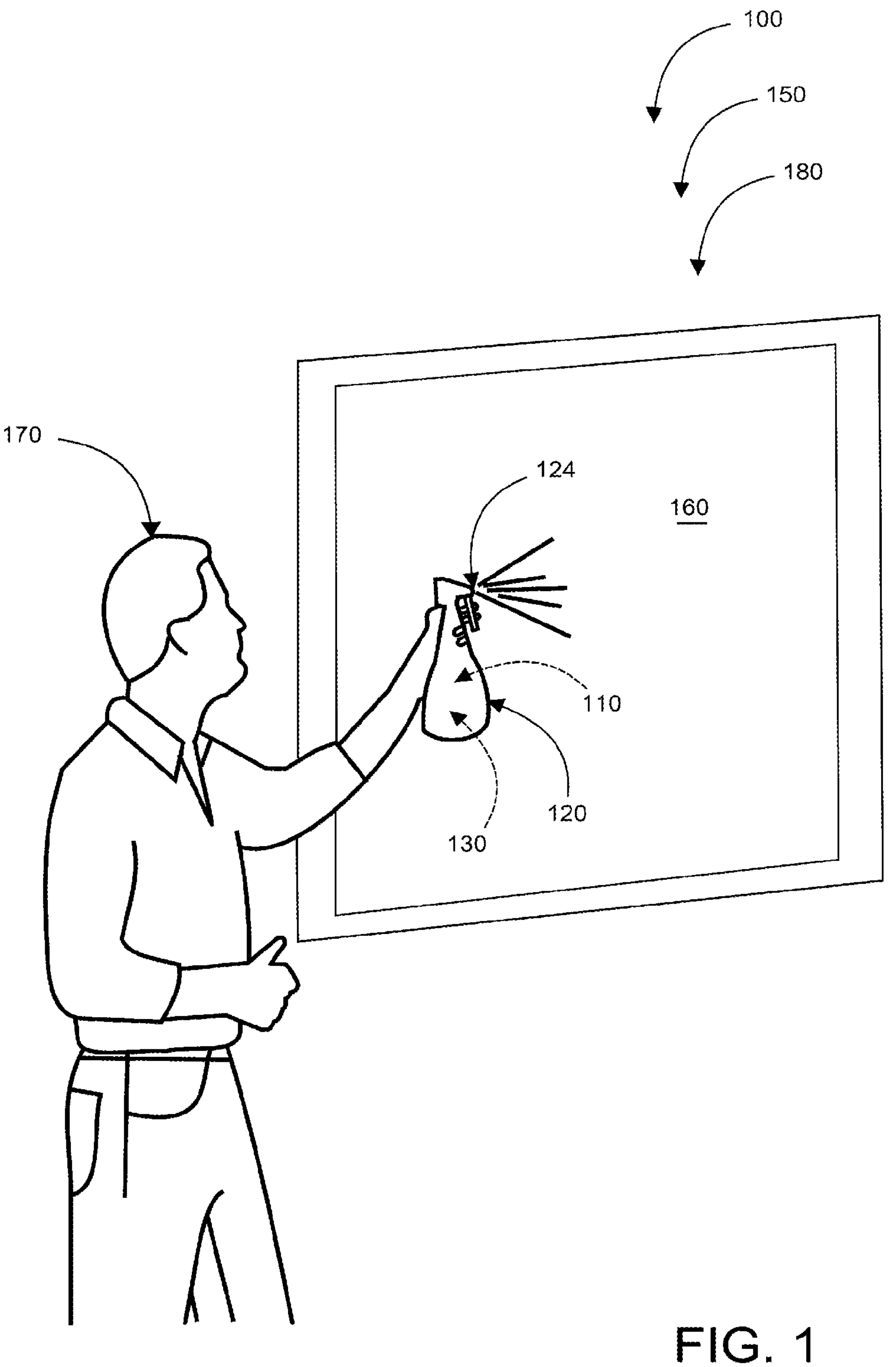
FIG. 1 shows a perspective view illustrating a sparkle essence system in an 'in-use' condition according to an embodiment of the present invention.

Referring now to FIG. 1 showing a perspective view illustrating sparkle essence system 100 in 'in-use' condition 150 according to an embodiment of the present invention Sparkle essence system 100 preferably comprises a plant based cleaning agent for household use 110. Sparkle essence system 100 further comprises at least one spray bottle 120 further comprising nozzle 124 in which to atomize-dispense cleaning agent 110. Plant based cleaning agent for household use 110 enables user 170 to thoroughly clean their homes without the risk of harming children, pets, or the environment. Further, plant based cleaning agent for household use 110 comprises all-natural plant ingredients and is void of harmful chemicals.

Plant based cleaning agent for household use 110 is preferably used on a variety of glass surfaces 160, such as home windows, car windows, glass headlights, television screens, computer screens, and may also be used on select surfaces comprising other materials.

Plant based cleaning agent for household 110 as disclosed herein comprises ingredients combined in proportions substantially including: 12 grams of pigeon pea leaves; and 2000 mL of distilled water.

Plant-based cleaning agent for household use 110 may be prepared by cutting and placing the pigeon pea leaves in a beaker comprising the volume aforementioned of distilled water to create homogenized mixture 130. The quantities given are for a preferred mixture but may be varied according to the desired potency of end product. The proportions given are relative to each other and if varying the total quantity of the finished product, one must be aware of the necessity to increase or decrease each ingredient proportionately.

When creating homogenized mixture 130 from pigeon pea leaves and distilled water, homogenized mixture 130 is preferably finish-homogenized in a centrifuge. Plant-based cleaning agent for household use 110 is preferably centrifuge-processed using the centrifuge at about 8,000 rpm for approximately ten minutes. When the centrifuge is used, a pellet is formed and is discarded so a newly formed extract is able to be stored at approximately 4 degrees C. for forty-eight hours to achieve stability. Stability is preferably achieved by putting the newly formed extract through a filter. The approximate size of the filter used is 0.45 um, however other sizes of filters may be used according to user-preference.

Plant based cleaning agent for household use 110 may be sealably stored in spray bottle 120. To use sparkle essence system 100, a handle on spray bottle 120 is depressed toward user 170 allowing atomized mist to be sprayed out nozzle 124. In this way the present invention may be applied to glass surface 160 where user 170 prefers plant based cleaning agent for household use 110 to spray a mist as shown in FIG. 1 and user 170 may wipe away excess plant based cleaning agent for household use 110 with a cloth or paper towel.

Sparkle essence system 100 according to an embodiment of the present invention of FIG. 1 may comprise kit 180. Kit 180 may comprise the following parts: plant-based household cleaner 110; at least one spray bottle 120; and a set of user instructions for making and using. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately such as at least one spray bottle, etc., may be sufficient.

Figure 2:
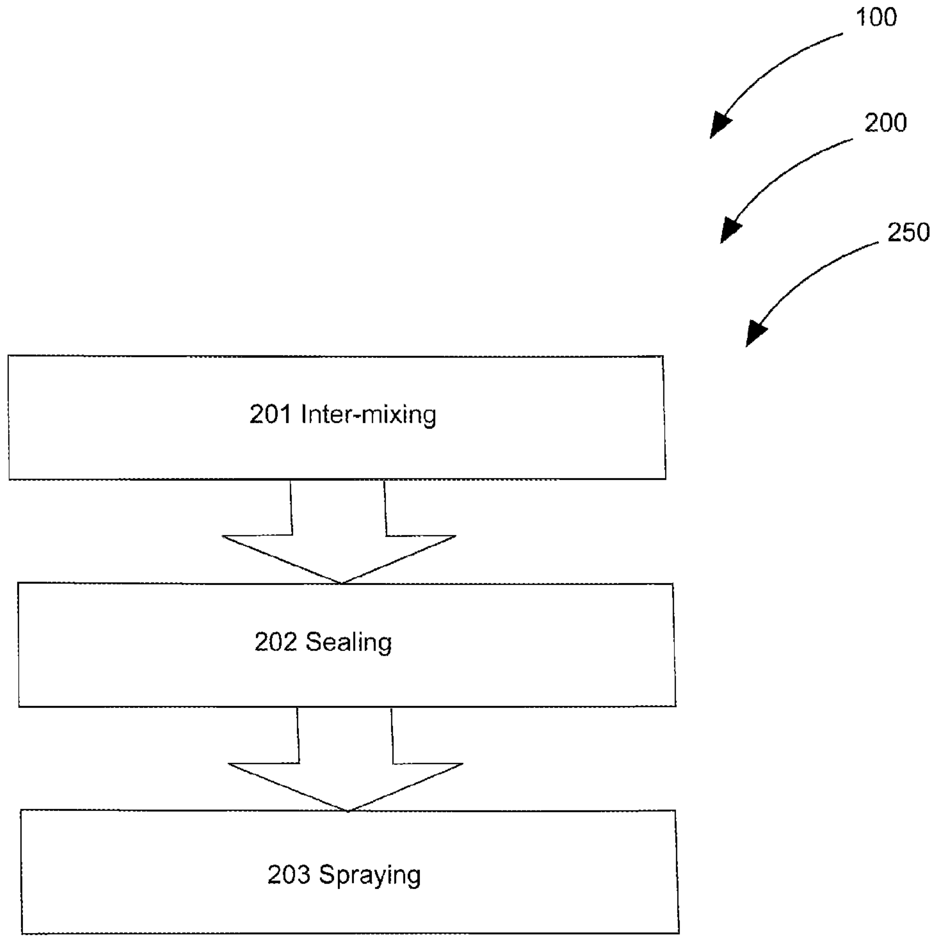
FIG. 2 is a flowchart illustrating a method of use according to an embodiment of the present invention of FIG. 1.

Referring now to FIG. 2. showing a flowchart 250 illustrating method of use 200 according to an embodiment of the present invention of FIG. 1. A method of producing plant-based household cleaner 110 comprises the steps of: step one 201 intermixing 12 g of pigeon pea leaves and 2000 mL of distilled water thereby producing mixture 130; step two 202 sealingly storing mixture 130 within at least one spray bottle 120; and step three 203 spraying plant-based household cleaner 110 using nozzle 124.

It should be noted that the steps described in the method of use can be carried out in many different orders according to user preference. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain mixing, storing steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A plant-based household cleaning product for cleaning household glass and/or other hard household surfaces comprising:
   - a. a homogenized mixture obtained from pigeon pea leaves;
   - b. a sealed spray bottle; and
   - c. a spray nozzle attached to the spray bottle for applying the homogenized mixture to the glass and/or other hard household surfaces;

wherein said homogenized mixture is obtained by a method comprising:

cutting 12 grams of the pigeon pea leaves and placing the cut leaves in 2000 mL of distilled water to create a mixture;

centrifuging the mixture to form a pellet;

cooling the mixture for a period of time; and filtering out the pellet from the mixture to form a homogenized mixture, wherein said homogenized mixture is stored in said spray bottle.

2. The plant-based household cleaning product according to claim 1, wherein said mixture is centrifuged at about 8,000 rpm for approximately ten minutes.

3. The plant-based household cleaning product according to claim 2, wherein said mixture is cooled at approximately 4° C. for about 48 hours.

4. The plant-based household cleaning product according to claim 3, wherein said pellet is filtered out with a 0.45 um filter.

5. A method for cleaning household glass and/or other hard household surface in need of cleaning, the method comprising spraying the household cleaning product according to claim 1 onto said glass and/or other hard household surface, and wiping the sprayed glass and/or household surface.

* * * * *